(12) United States Patent
Groman (10) Patent No.: US 8,668,552 B2
(45) Date of Patent: Mar. 11, 2014

(54) METHODS OF MAKING MICRO-ABRASIVE BLASTING DEVICE FOR DENTAL APPLICATIONS

(71) Applicant: Boaz Barry Groman, Boca Raton, FL (US)

(72) Inventor: Boaz Barry Groman, Boca Raton, FL (US)

( * ) Notice: Subject to any disclaimer, the term of this patent is extended or adjusted under 35 U.S.C. 154(b) by 4 days.

(21) Appl. No.: 13/773,638

(22) Filed: Feb. 22, 2013

(65) Prior Publication Data

US 2013/0160275 A1 Jun. 27, 2013

Related U.S. Application Data

(62) Division of application No. 13/553,766, filed on Jul. 19, 2012, which is a division of application No. 12/551,416, filed on Aug. 31, 2009, now Pat. No. 8,241,094, which is a division of application No. 11/452,067, filed on Jun. 13, 2006, now Pat. No. 7,607,972.

(51) Int. Cl.
*B24C 5/02* (2006.01)

(52) U.S. Cl.
USPC .................................. 451/38; 451/90

(58) Field of Classification Search
USPC .............. 451/90, 99, 102, 75, 38, 39, 40
See application file for complete search history.

(56) References Cited

U.S. PATENT DOCUMENTS

| | | | | |
|---|---|---|---|---|
| 2,423,173 A * | 7/1947 | Brady et al. | ............... | 73/864.02 |
| 4,475,370 A * | 10/1984 | Stark et al. | ......................... | 72/53 |
| 5,199,229 A * | 4/1993 | Herold et al. | ................. | 451/102 |
| 6,343,717 B1 * | 2/2002 | Zhang et al. | .................. | 222/209 |
| 7,607,972 B2 * | 10/2009 | Groman | ........................ | 451/102 |
| 8,241,094 B2 * | 8/2012 | Groman | ......................... | 451/38 |

* cited by examiner

*Primary Examiner* — Robert Rose
(74) *Attorney, Agent, or Firm* — Gerald E Linden (57) ABSTRACT

A micro-abrasive blasting device comprises a mixing chamber, a delivery conduit extending from external the mixing chamber to the mixing chamber and a discharge conduit extending from the mixing chamber. Abrasive material may selectively be sealed in the chamber by positioning the discharge conduit to abut the inlet port. The chamber may be spherical to deliver consistent powder perturbation at all mixing chamber orientations. Methods of using the device are disclosed. Methods of making the device by blow molding are disclosed.

9 Claims, 10 Drawing Sheets

METHODS OF MAKING MICRO-ABRASIVE BLASTING DEVICE FOR DENTAL APPLICATIONS

CROSS-REFERENCE TO RELATED APPLICATIONS

This is a division of Ser. No. 13/553,766 filed Jul. 19, 2012, which is a division of U.S. Ser. No. 12/551,416 filed Aug. 31, 2009 (now U.S. Pat. No. 8,241,094), which is a division of U.S. Ser. No. 11/452,067 filed Jun. 13, 2006 (now U.S. Pat. No. 7,607,972), all by Groman.

FIELD

The invention relates generally to the field of devices for propelling abrasive powder with intent to etch the surface of a target material. More specifically, the present invention relates to a micro-abrasive blasting device powered by a pressurized-gas source for use with dental procedures.

BACKGROUND

Abrasive blasting devices operate on the physical property that gas at a higher pressure flows towards and into gas at lower pressure. When abrasive powder is mixed with gas at higher pressure, the gas carries the abrasive powder as the gas accelerates and flows to the lower pressure. As the gas and abrasive powder blast the target material at high speed, the impact of the particles removes layers of the target material.

In dentistry this technology is known as micro-abrasion and is used to achieve a variety of goals—such as to remove foreign material or to dull a shiny surface, roughen or etch the surface to enhance bonding quality and to remove decay by drilling and cutting tooth structure.

Air abrasion devices date back decades with patented inventions by pioneers such as Ziegler U.S. Pat. No. 2,612,732, Crow U.S. Pat. No. 2,725,684, Schachter U.S. Pat. No. 3,626,841 and Paache U.S. Pat. No. 2,441,441.

Over the years two main approaches to air abrasion devices developed with Ziegler and Schechter following one approach and Crowe and Passche following another. One approach has been to provide a stationary mixing apparatus for generating the abrasive laden air stream and delivering the abrasive laden air stream through an extended hand-piece for directing the stream onto the target surface. Another approach has been to integrate the mixing apparatus into the hand-held device.

The first approach facilitates more complex mechanisms and many operational options since the size and weight of the device are of no concern. Because the extended hand-piece delivers the abrasive laden air stream independent of the mixing operation, the hand-piece can be held at any orientation during operation. Deardon et al. U.S. Pat. No. 6,083,001 discloses a dental air abrasion system in which the flow of the particles is electronically controlled by pressure differentials. Rainey U.S. Pat. No. 6,093,021 discloses an automated control system which utilizes a gas stream mounted particulate sensor to regulate fluid flow rates into and around the ultrasonically agitated mixing chamber in order to accurately maintain the abrasive concentration in the air stream. Various methods for reducing the overspray of the abrasive have also been developed for these devices. Ho U.S. Pat. No. 5,356,292, Coston U.S. Pat. No. 5,197,876, and Burns et al. U.S. Pat. No. 6,024,566 disclose add-on splatter guard and collector attachments to air abrasion devices.

In the second approach, the size, weight, and ergonomic shape of the device are significant factors. Herald et al. U.S. Pat. No. 5,199,299 and Burns et al. U.S. Pat. No. 6,439,966 disclose innovative hand-holdable air abrasion devices which mount the mixing apparatus into the hand-piece. The drawback of this approach is that the operation of these devices is limited by the orientation of the mixing chamber.

An adjunct to the second approach has been the concept of simple self-contained air abrasion devices—such as Hertz U.S. Pat. No. 5,839,946 (and its derivative U.S. Pat. No. 6,287,180, U.S. Pat. No. 6,951,505, and Granted Appl. No. 09/939,865), Groman U.S. Pat. No. 6,398,628 (and its derivative U.S. Pat. No. 6,347,984 and Pending application Ser. No. 10/144,228), Schur et al. U.S. Pat. No. 6,004,191, and Trafton et al. U.S. Pat. No. 6,354,924. These devices rely on the air stream to perturb the abrasive and generate the mixing action based on Stark et al. U.S. Pat. No. 4,475,370 fixed air abrasion device for treating dental castings.

Merging of Stark's blow-through mixing method into the hand-piece so the mixing chamber is held between the user's fingers has taken air abrasion art to a new level. Because of their simplified structures, simple self-contained air abrasion devices tend to be less expensive to manufacture and can therefore be marketed to the user as disposable instruments.

With increased emphasis in Medical, Pharmaceutical, Cosmetic and Dental applications on reduced cross-patient contamination, there has been a significant drive towards single usage disposable packaging and devices. With advances in materials and fabrication technologies the cost of these devices has been significantly reduced. Dougherty U.S. Pat. No. 4,391,590 discloses a syringe and stopper like cartridge device for dispensing material while Hertz U.S. Pat. No. 5,839,946 patent discloses the formulation an air abrasion instrument from a syringe and stopper type structure. Both innovations capitalize on the lower cost of fabrication and the well established production methods of a syringe and stopper configuration.

Simple self-contained prior art air abrasion devices support an elongated cylindrical chamber with an inlet conduit for delivering the air into the mixing chamber and a discharge conduit for carrying the air-abrasive mixture out of the mixing chamber. The mixing chambers are utilized as a reservoir for storing the abrasive powder. Once the reservoir is depleted of abrasive material, the devices are discarded and therefore function as disposable instruments which do not require sterilization post intra-oral use.

To prevent the abrasive material from escaping the mixing chamber or becoming contaminated prior to use, simple self-contained prior art air abrasion devices add additional components which seal the inlet and outlet ports and conduits. While the Hertz U.S. Pat. No. 5,839,946, and Schur et al. U.S. Pat. No. 6,004,191 devices include passive caps which must be removed prior to using the instrument, Hertz U.S. Pat. No. 6,951,505 and U.S. Pat. No. 6,287,180, and Groman U.S. Pat. No. 6,398,628 and U.S. Pat. No. 6,347,984 add functional components which actively prevent the abrasive from exiting the mixing chamber. Groman U.S. Pat. No. 6,398,628 has a filter that prevents the abrasive from exiting the device's inlet port and a movable discharge conduit which prevents abrasive material from exiting the mixing chamber when the discharge conduit inlet port abuts the side wall of the mixing chamber. Groman pending application Ser. No. 10/144,228 support a deformable gasket at the discharge port internal to the mixing chamber which opens when flow is present. Hertz U.S. Pat. No. 6,951,505 has a deformable seal at the inlet port external to the mixing chamber which functions as a check-valve that allows the pressurized-gas to enter the instrument but prevents abrasive from exiting the instrument. Groman U.S. Pat. No. 6,398,628 discloses a deformable and movable cap configurations which block both the delivery conduit inlet and discharge conduit outlet prior to use.

Another disposable delivery method disclosed by Zhang et al. U.S. Pat. No. 6,343,717 attempts to address the containment of stored material utilizing a pipette structure. A typical pipette consists of a slender pipe or tube that is used to transfer or measure small quantities of material from one location to another. The most common type of pipette consists of a small tube that widens into a bulb at the middle.

Zhang et al. pipette structure is made of a rigid or resilient material that is pre-filled with a pharmaceutical or cosmetic product and is used once and then discarded. Zhang et al. discloses a plurality of ways by which the disposable pipette can be sealed to contain the material and then unsealed by the user prior to use for dispensing the stored material. According to Zhang's et al. invention the majority of material is retained within the bulb section of the pipette, but Zhang's et al. sealing methods permit the contained material to migrate into the top and bottom tube sections. Although Zhang's et al. use of a pipette structure leads to a very cost effective means of delivering the contained material, Zhang's et al. sealing methods are not compatible with the needs of air abrasion devices.

Pressurized air stream is delivered to the simple self-contained air abrasion devices of Hertz, Groman, Schur, and Trafton via custom connectors which engage the device externally and to form a seal with the device body to deliver the pressurized air to the mixing chamber delivery port. The connectors are designed to supply clean dry air in order to maintain the abrasive powder dry, since any moisture causes clumping of the abrasive material and therefore the malfunction of the device. The dry air is required because the gas delivery conduit leads directly into the mixing chamber; therefore any liquid present at the entry to the device gets trapped in the mixing chamber. Hertz et al. U.S. Pat. No. 6,293,856 discloses a connector with additional conduits for carrying other types of fluids passively through the mixing chamber. This configuration requires a very complex connector to assure the separation of the fluids delivered to the air abrasion instrument without contaminating the mixing chamber. Custom connectors which supply dry air add to the installation cost and complexity of these disposable devices. And because they attach to the body of the devices, these connectors are typically very bulky.

Figure 1A:
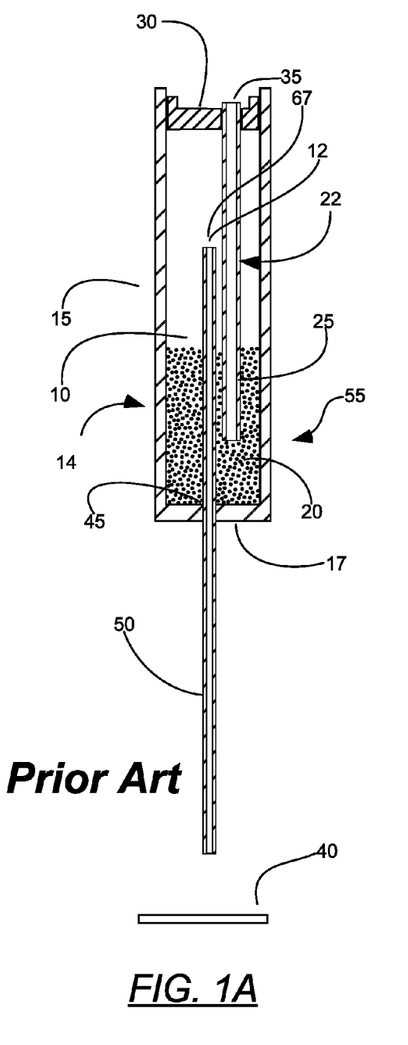
Figure 1B:
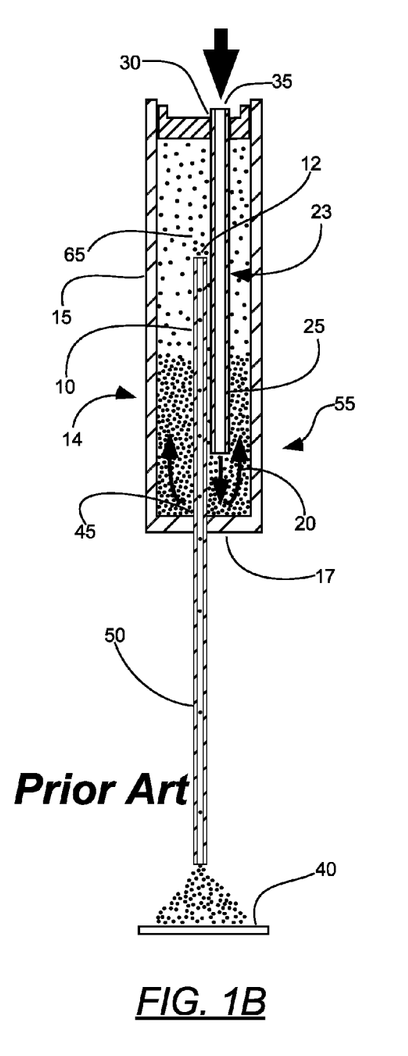

Referring to FIG. 1, prior art self-contained air abrasion devices use a blow-through methodology to agitate the abrasive powder. More specifically, these devices utilize the delivery conduit to deliver the gas stream into the abrasive material. As the gas stream blows through the abrasive material, the abrasive material is agitated. Gravity is utilized to assure that the non-aerated abrasive remains at the bottom of the mixing chamber. As the air stream reverses direction towards the discharge conduit inlet, aerated particles are captured by the air stream. The abrasive laden air stream is pushed out of the mixing chamber through the discharge conduit by the higher pressure gas source.

In their reduction to practice, both the Schur and Groman devices require the user to maintain the orientation of the device so the mixing chamber points downward. The attached user instructions for the Schur and Groman devices outline the specific user instructions cautioning the user about misorienting the mixing chamber. To compensate for his shortcoming, the marketed Groman instrument provides a finger bendable discharge conduit. The marketed Schur device provides a bending tool, so the user is able to form the delivery conduit to reach upper surfaces while maintaining the proper orientation of the mixing chamber.

Figure 2:
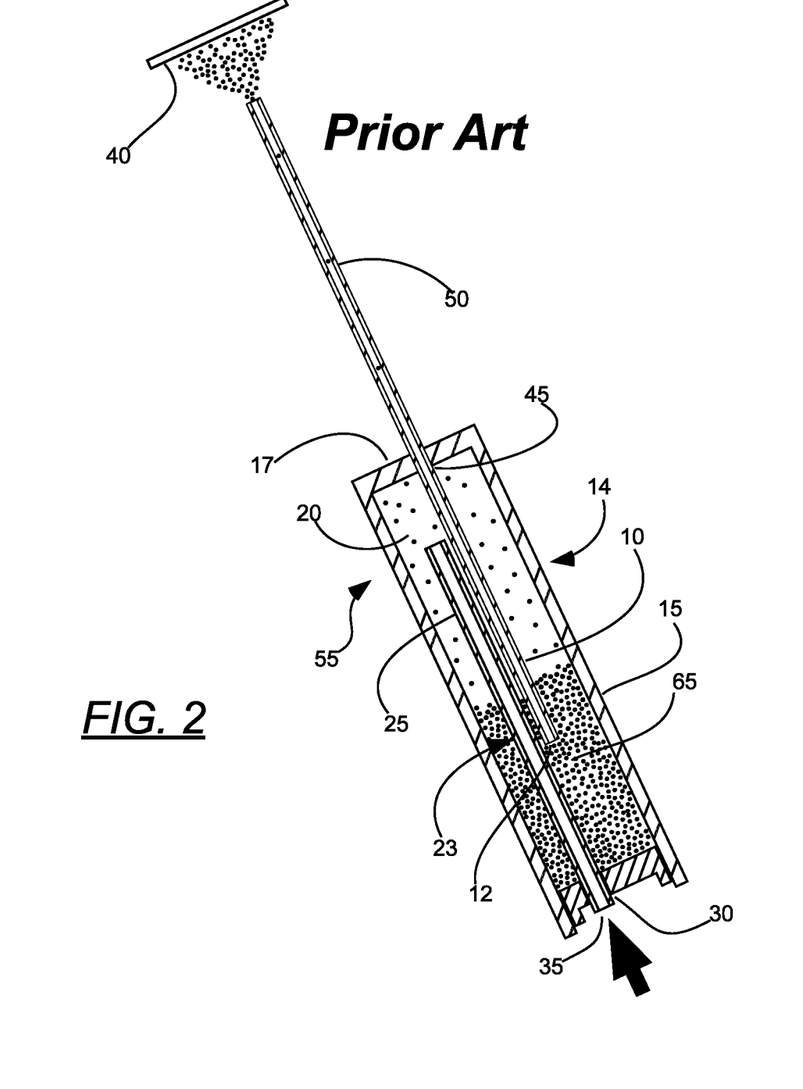

Referring to FIG. 2, if the user attempts to utilize these prior art devices with the mixing chamber horizontal or upside down, the abrasive material is pushed directly into the discharge conduit without being properly mixed with the air steam. This leads to a concentration of abrasive material to exit the device in an uncontrolled manner, which creates a cloud of abrasive dust or clogs up the discharge conduit as the abrasive powder binds. Additionally, in certain orientations the delivery conduit is not immersed in the abrasive material which also disrupts the mixing operation of these prior art devices. In fact, the pressurized-gas exiting the delivery conduit creates a back pressure on the abrasive within the mixing chamber causing the abrasive powder particles to bind together instead of mix with the air stream. Most importantly, these disruption in flow can lead to a defective clinical procedure which either under or over etches the target tooth surface.

SUMMARY

The invention disclosed herein addresses the following shortcomings with the prior art simple self-contained air abrasion devices:
1) Eliminates the need for the inlet and outlet caps or other sealing methods.
2) Makes the device insensitive to liquids at the pressurized-gas connection.
3) Makes the air abrasive mixing operation independent of the orientation of the mixing chamber.
4) Eliminates back pressure buildup within the mixing chamber.
5) Eliminates the need for a bulky custom connection to the instrument for pressurized-gas delivery.

In addition, this invention teaches a new innovative method for constructing the air abrasion device out of a continuous tubing formed into a disposable pipette structure.

Accordingly, several objects and advantages of the present invention(s) may include to:
1) Reduce component count by utilizing the discharge conduit in conjunction with the delivery conduit inlet to seal the abrasive material within the mixing chamber.
2) Create a bypass to the mixing chamber so liquids in the pressurized-gas connection are purged out of the system without contaminating the abrasive within the mixing chamber.
3) Provide a spherical mixing chamber which assures a distal separation between the discharge conduit inlet and the abrasive powder at all mixing chamber orientations.
4) Eliminate the air stream reversal within the mixing chamber so back pressure is never created on the abrasive powder.
5) Extend the delivery conduit external to the mixing chamber so a slender handheld gas supply connector and standard tube fittings can be utilized for pressurized-gas delivery.
6) Make the disposable pipette structure usable for air abrasion applications in order to further reduce the manufacturing costs.

Still another object of the invention is that the material in the bulb of the pre-filled pipette is protected from contamination or spillage by the discharge conduit.

A micro-abrasive blasting device constructed from a disposable pipette structure comprising a delivery conduit extending from a delivery conduit inlet through a tapered section to form a delivery conduit outlet and a inlet port; contiguous pipette structure expands from inlet port to form a hollow bulb mixing chamber and then narrows to form a discharge port section; a discharge conduit is in fluid communications with discharge port and extends from a discharge conduit inlet internal to mixing chamber to a discharge conduit outlet external to mixing chamber; a particulate matter is disposed within mixing chamber wall; discharge conduit inlet abuts inlet port preventing particulate matter from exiting mixing chamber. A separation gap between the delivery conduit outlet and discharge conduit inlet is created as discharge conduit is displaced so discharge conduit inlet no longer abuts inlet port; As pressurized-gas is supplied to micro-abrasive blasting device through the delivery conduit inlet, the pressurized-gas flows through the delivery conduit and out of the inlet port, into mixing chamber. As flow is initiated, particulate matter instantaneously mixes with the gas-steam within hollow resilient bulb mixing chamber and the powder-gas mixture flows through discharge conduit to strike target surface.

BRIEF DESCRIPTION OF THE DRAWINGS

Various other objects, advantages, and features of the invention will become apparent to those skilled in the art from the following discussion taken in conjunction with the following drawings, where closely related figures have the same number but different alphabetic suffixes:

FIGS. 1 (1A, 1B) and 2 are views of prior art micro-abrasive blasting devices.

FIGS. 3 (3A, 3B, 3C) are cross-sectional views of the innovative micro-abrasive blasting device and isometric view of the innovative device mounted into a handpiece connector.

FIGS. 4 (4A, 4B) are cross-sectional views of the innovative micro-abrasive blasting device fabricated out of a pipette structure.

FIGS. 5 (5A, 5B) and 6 (6A, 6B, 6C) are isometric and cross-sectional views of micro-abrasive blasting devices with spherical mixing chamber.

FIGS. 7 (7A, 7B) are cross-sectional views of an embodiment of the micro-abrasive blasting device with discharge conduit bearing integral to the pipette structure.

REFERENCE NUMERALS IN DRAWINGS 10 discharge conduit
12 discharge conduit inlet
14 discharge conduit outlet
23 mixing chamber
25 mixing chamber wall
27 inlet port
29 discharge port
30 delivery conduit
32 delivery conduit external section
33 delivery conduit tapered section
34 delivery conduit internal section
35 delivery conduit inlet
37 delivery conduit outlet
40 target surface
45 separation gap
48 pressure gradient
50 particulate matter
55 handheld supply connector
75 micro-abrasive blasting device
80 pipette structure
82 discharge conduit bearing 83 Discharge conduit stop
85 protective nozzle guard
87 nozzle guard separation point
90 particle deflector
93 particle deflector separation point
95 capped position end
97 mixing position end

DETAILED DESCRIPTION

It is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES (FIGs.) are designated by the same reference numerals.

First Embodiment

Referring to FIG. 3, a micro-abrasive blasting device 75 is disclosed; Micro-abrasive blasting device 75 comprises a mixing chamber 23 formed by a mixing chamber wall 25 and supports a inlet port 27 and a discharge port 29; a delivery conduit 30 extending from a delivery conduit inlet 35 external to mixing chamber 23 to a delivery conduit outlet 37 internal to mixing chamber 23, by means of protruding into mixing chamber 23 through mixing chamber wall 25 at inlet port 27; a discharge conduit 10 is in fluid communications with mixing chamber 23 at discharge port 29, and extending from a discharge conduit inlet 12 internal to mixing chamber 23 to a discharge conduit outlet 14 external to mixing chamber 23; a particulate matter 50 is disposed within mixing chamber 23.

Figure 3A:
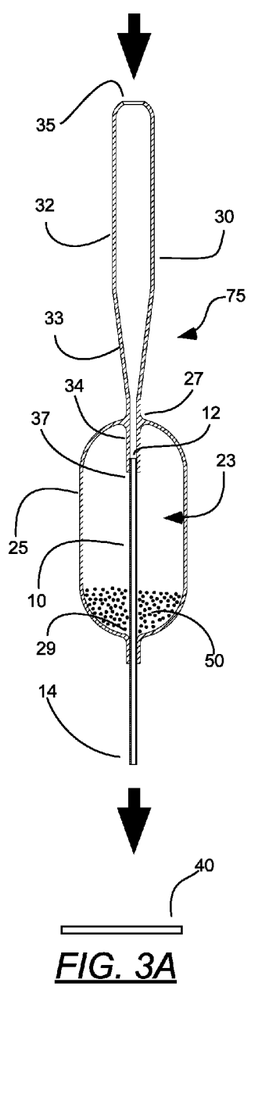
Figure 3B:
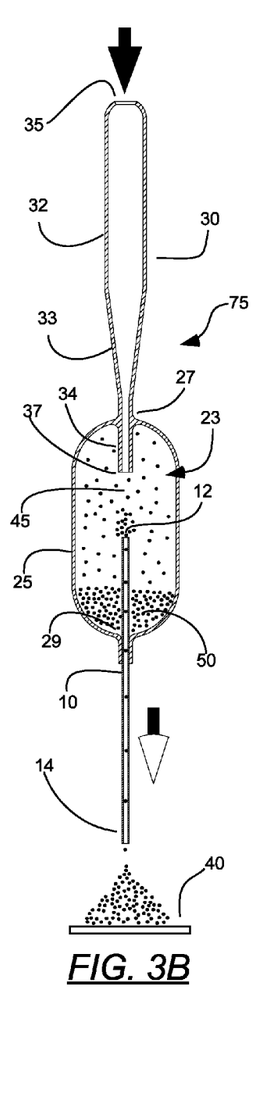
Figure 3C:
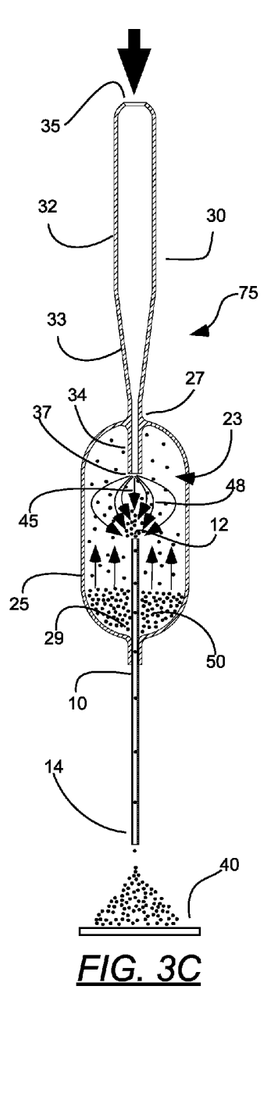

Delivery conduit 30 comprises a delivery conduit external section 32 external to mixing chamber 23 and a delivery conduit internal section 34 internal to mixing chamber 23 and a connecting delivery conduit tapered section 33; external section 32 of delivery conduit 30 is preferably straight and preferably supports an outer and inner diameter that fits into standard tube and hose connectors such as push-in or push-on connector types; internal section 34 of delivery conduit 30 preferably supports an inner diameter that is equivalent to the outer diameter of discharge conduit inlet 12.

Figure 3D:
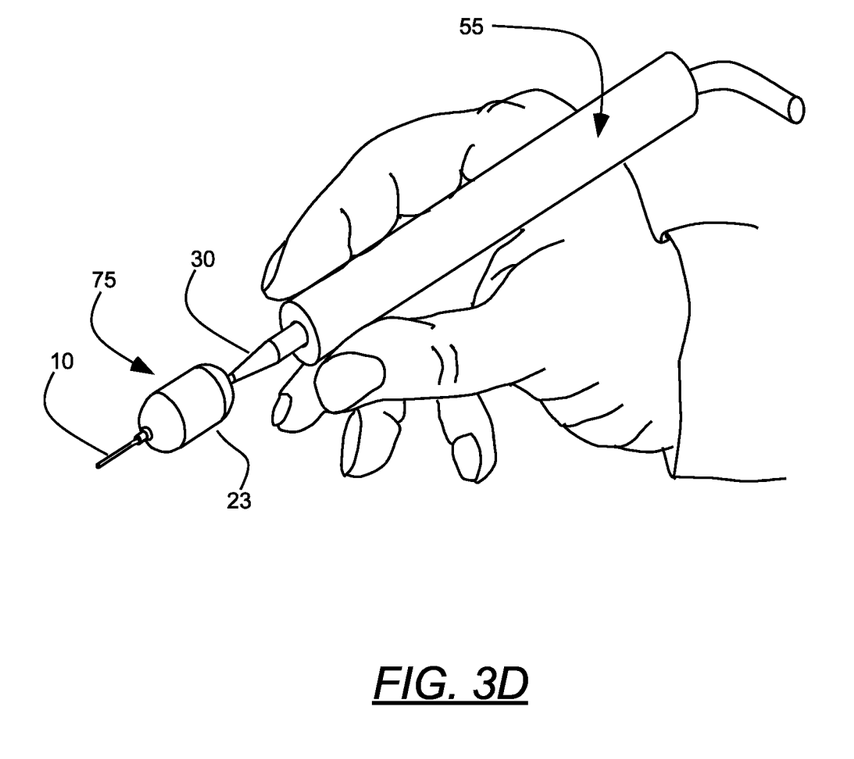
FIG. 3D is a perspective view.

Referring to FIG. 3D, extending delivery conduit 30 external to the mixing chamber 23 facilitates a connection to a handheld pressurized-gas supply connector 55. Not only does this innovative configuration simplify the type of connection required for supplying the pressurized-gas and therefore the cost of the air supply adaptor, it also facilitates a more narrow connection to the air abrasion device. Whereas, prior art devices connect to the mixing chamber body, this embodiment connects to a narrower delivery conduit. Therefore, the innovative micro-abrasive blasting device 75 may be mounted as a disposable tip onto a non-disposable handheld supply connector 55. While handheld supply connector 55 is held by the user's fingertips, delivery conduit 30 of micro-abrasive blasting device 75 mounts into handheld supply connector 55 downstream of the user's fingertips. Because the innovative micro-abrasive blasting device 75 does not support the user's grip and bulky supply connector, micro-abrasive blasting device 75 can be made shorter and of less rigid material. This configuration greatly decreases the complexity and cost of the micro-abrasive blasting device 75.

Referring to FIG. 3A, discharge conduit inlet 12 abuts delivery conduit outlet 37 as to prevent particulate matter 50 from exiting mixing chamber 23, thereby sealing particulate matter 50 within mixing chamber 23. As delivery conduit external section 32 engages with a pressurized-gas source, pressurized-gas is delivered to delivery conduit 30 at delivery conduit inlet 35; the pressurized-gas passes through delivery conduit 30 into discharge conduit 10 to exit micro-abrasive blasting device 75 at discharge conduit outlet 14. Since discharge conduit inlet 12 abuts delivery conduit outlet 37 the pressurized gas can not enter mixing chamber 23. Therefore, any moisture or liquid residue contained in or carried by the pressurized-gas does not enter mixing chamber 23 and is discharged through micro-abrasive blasting device 75.

Referring to FIG. 3B, a separation gap 45 between the delivery conduit outlet 37 and discharge conduit inlet 12 is created as discharge conduit 10 is displaced so discharge conduit inlet 12 no longer abuts delivery conduit outlet 37; As pressurized-gas is supplied to micro-abrasive blasting device 75 through delivery conduit inlet 35, the pressurized-gas flows through delivery conduit 30 and out of delivery conduit outlet 37 into mixing chamber 23. When gas flow is present, particulate matter 50 instantaneously mixes with the flowing gas and is dispensed through discharge conduit 10 to strike target surface 40. Once mixing chamber 23 is depleted of particulate matter 50, micro-abrasive blasting device 75 is removed from the pressurized-gas source and discarded.

Second Embodiment

Figure 4A:
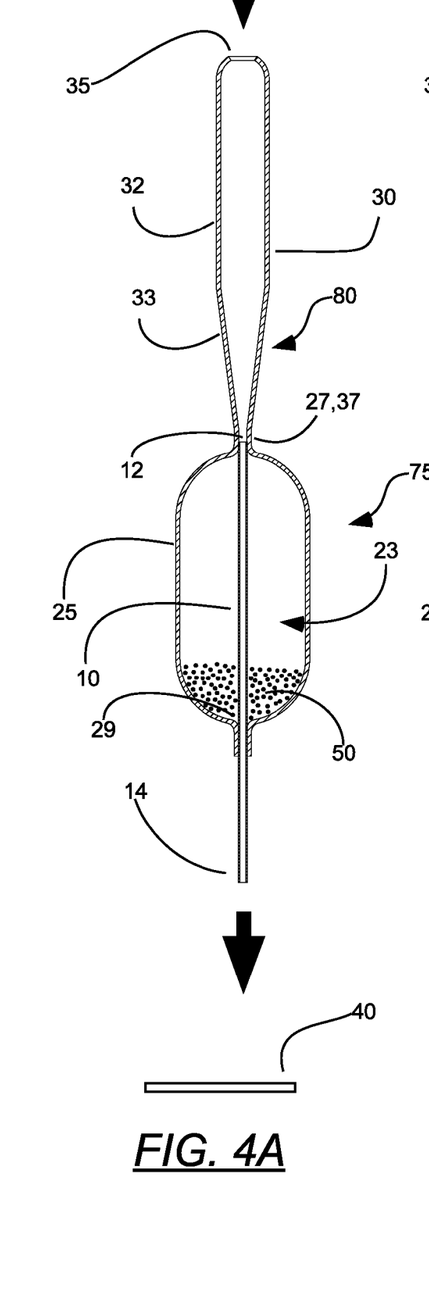
Figure 4B:
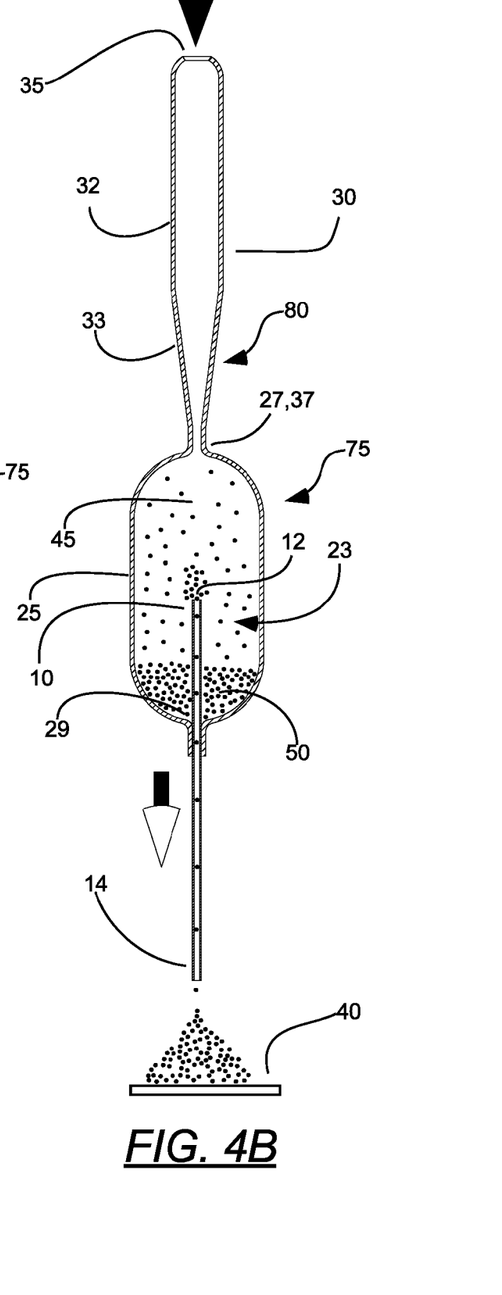

Referring to FIG. 4, a micro-abrasive blasting device 75 is comprised of a hollow resilient round tubular pipette structure 80 constructed of a thermoplastic material such as polycarbonate, polyethylene, polyester, polystyrene, polypropylene, polysulfone, polyurethane, ethylene-vinyl-acetate or the like. The material may be transparent, translucent, opaque, or pigmented to indicate the type of abrasive powder contained within the sealed mixing chamber. Pipette structure 80 preferably has a circular cross section but can also be fabricated out of other cross sectional shapes.

Micro-abrasive blasting device 75 is comprised of a pipette structure 80 which consists of three sections, a hollow bulb section forming a mixing chamber 23; a open ended hollow tubular delivery conduit 30 section smaller in diameter and contiguous with the bulb section at inlet port 27, for delivery of pressurized-gas; a hollow tubular discharge port 29 section smaller in diameter and contiguous with the bulb section, for discharging abrasive laden gas stream; a discharge conduit 10 in fluid communications with discharge port 29, and extending from a discharge conduit inlet 12 internal to mixing chamber 23 to a discharge conduit outlet 14 external to mixing chamber 23; a particulate matter 50 is disposed within mixing chamber 23. Preferably, delivery conduit 30 section extends from a delivery conduit inlet 35 through a external section 32 and a tapered section 33 to form a delivery conduit outlet 37 and a inlet port 27.

The outer and/or inner diameter of delivery conduit external section 32 is preferably selected to fit standard tube or hose fittings, while the inner diameters of inlet port 27 and discharge port 29 preferably support an inner diameter that is equivalent to or less than the outer diameter of discharge conduit 10. Design selections of these diameters may eliminate or reverse the gradient of delivery conduit tapered section 33, rendering delivery conduit 30 a straight tube. The diameter of hollow resilient bulb mixing chamber 23 is preferably selected to support the appropriate quantity of particulate matter 50 to at least perform one dental procedure.

Pipette structure 80 may be formed via blow-molding and/or tube swaging techniques, or other thermo-forming processes. These methods would typically require that one of the ends of the tubular pipette structure 80 be sealed in order to entrap pressurized-gas for forming the component during the blow-molding process. The sealed end may be formed at the delivery conduit inlet 35 of delivery conduit 30 section or at the tip of discharge port 29 section. The sealed end may be trimmed off during the assembly process of micro-abrasive blasting device 75 or just punctured or cut to permit air flow into micro-abrasive blasting device 75 when mounted onto a pressurized-gas connector. Additionally, the pressurized-gas connector could support cutting or puncturing means for breaking the blow-molded seal when delivery conduit 30 is mounted on the pressurized-gas connector.

Referring to FIG. 4A, discharge conduit inlet 12 fits within or abuts inlet port 27 preventing particulate matter 50 from exiting mixing chamber 23. As delivery conduit external section 32 engages with a pressurized-gas source, pressurized-gas is delivered to delivery conduit 30 at delivery conduit inlet 35; the pressurized-gas passes through delivery conduit 30 into discharge conduit 10 to exit micro-abrasive blasting device 75 at discharge conduit outlet 14. Since discharge conduit inlet 12 abuts inlet port 27 the pressurized gas can not enter mixing chamber 23.

Referring to FIG. 4B, a separation gap 45 between the inlet port 27 and discharge conduit inlet 12 is created as discharge conduit 10 is displaced so discharge conduit inlet 12 no longer abuts inlet port 27; As pressurized-gas is supplied to micro-abrasive blasting device 75 through delivery conduit inlet 35, the pressurized-gas flows through delivery conduit 30 and out of inlet port 27, into mixing chamber 23. As flow is initiated, particulate matter 50 instantaneously mixes with the gas-steam within hollow resilient bulb mixing chamber 23 and the powder-gas mixture flows through discharge conduit 10 to strike target surface 40.

Third Embodiment

Figure 5A:
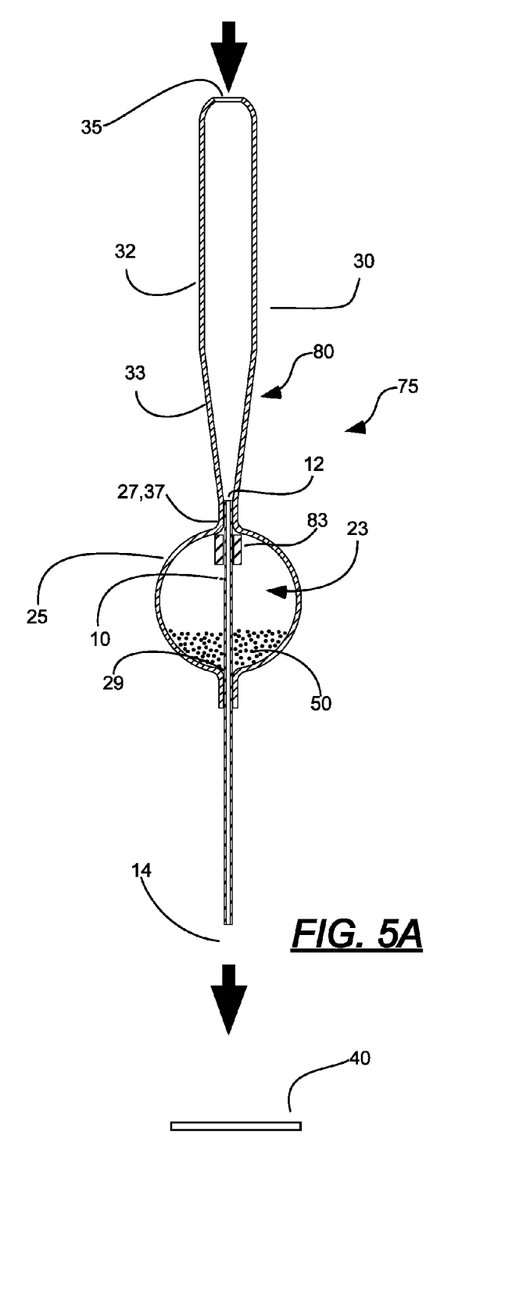
Figure 5B:
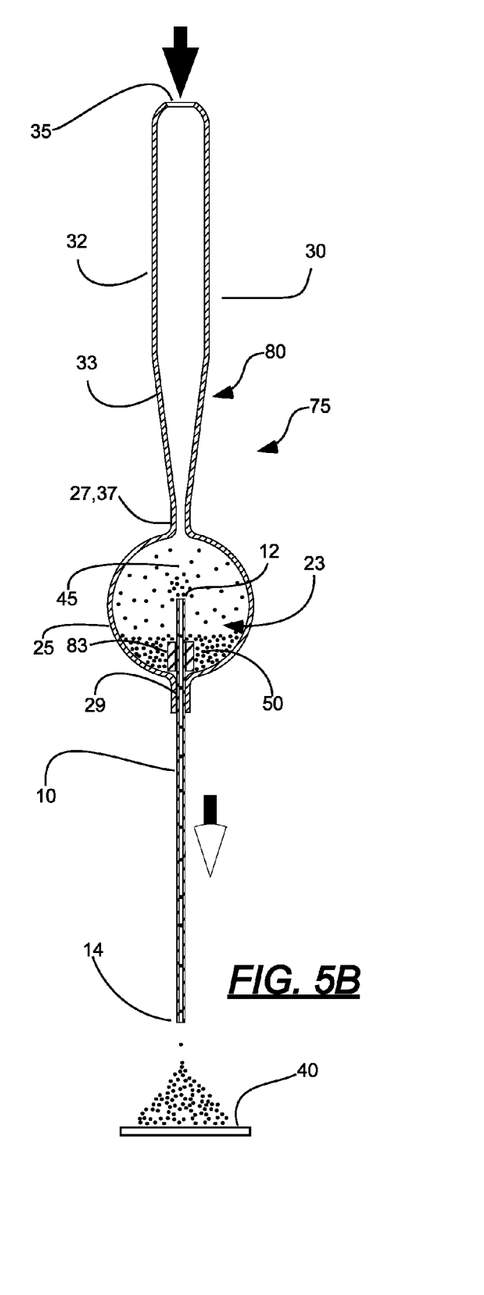
Figure 5C:
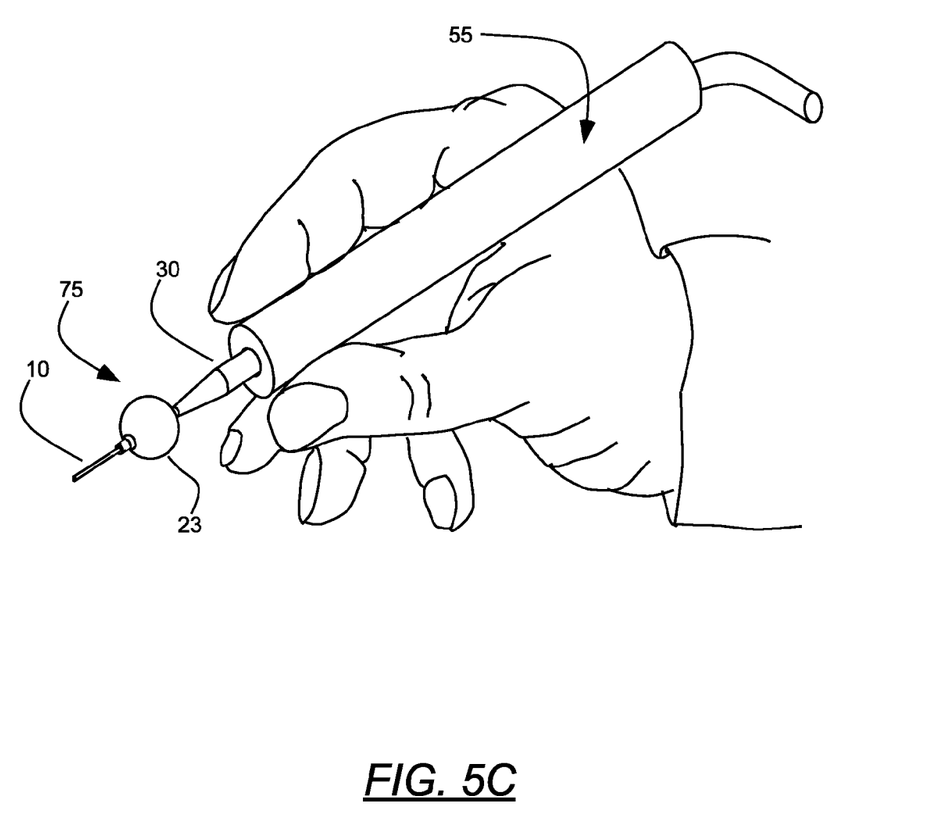
FIG. 5C is a perspective view.

Referring to FIG. 5, this preferred micro-abrasive blasting device 75 is also constructed of a contiguous pipette structure 80 and operates as the preferred embodiments of FIGS. 3 and 4. However, pipette structure 80 of the FIG. 5 embodiment supports a mixing chamber wall 25 constructed to form a hollow spherical bulb mixing chamber 23. The spherical shape of mixing chamber 23 assures a distal separation between the discharge conduit inlet 12 and the particulate matter 50 at all orientations of mixing chamber 23.

Figure 6A:
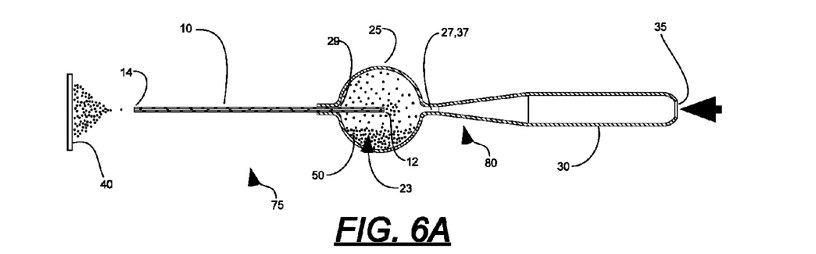

Referring to FIG. 6A, when micro-abrasive blasting device 75 is operated in a horizontal orientation, particulate matter 50 is pulled by gravity to the mixing chamber wall 25 at the bottom surface of mixing chamber 23. Therefore, during operation, the spherical configuration of mixing chamber 23 keeps particulate matter 50 distant from discharge conduit inlet 12, thereby maintaining the proper mixing action.

Figure 6B:
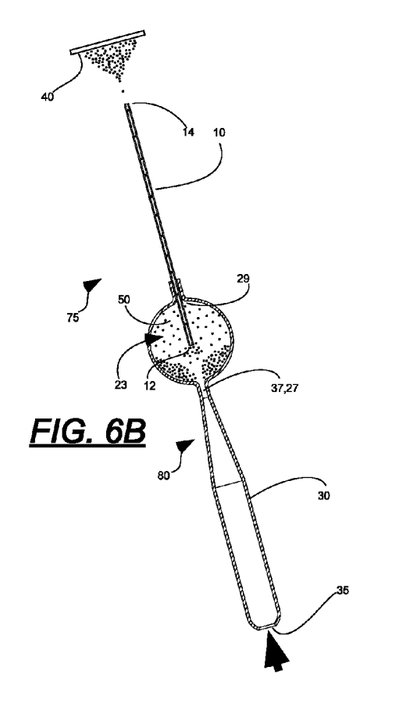
Figure 6C:
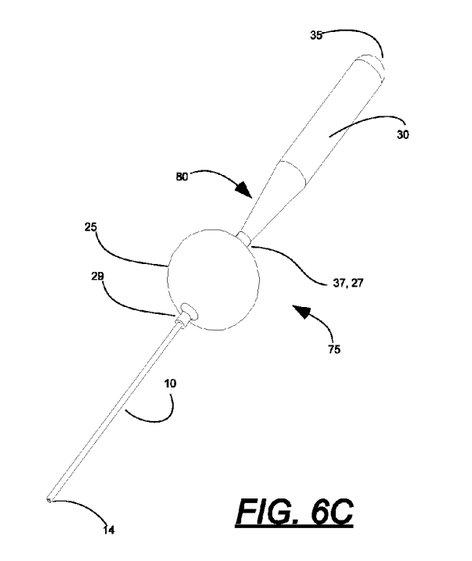

Referring to FIG. 6B, when micro-abrasive blasting device 75 is operated in a vertical orientation, the spherical shape of mixing chamber 23 also assures a distal separation between the discharge conduit inlet 12 and the particulate matter 50 at all mixing chamber 23 orientations. Additionally, the elimination of the delivery conduit internal section—referred to in the embodiment of FIG. 3 as delivery conduit internal section 34—assures that the pressurized gas stream entering mixing chamber 23 at inlet port 27 always directs the pressurized-gas into particulate matter 50 thereby eliminating the potential for back pressure on particulate matter 50.

Referring to FIG. 5, a discharge conduit stop 83 is attached to discharge conduit 10 so discharge conduit stop 83 moves with discharge conduit 10 within mixing chamber 23 from inlet port 27 to discharge port 29. Discharge conduit stop 83 provides a mechanical restriction to the displacement of discharge conduit 10 by creating a restriction at inlet port 27 and discharge port 29. When discharge conduit stop 83 abuts inlet port 27, discharge conduit inlet 12 is properly positioned to seal mixing chamber 23. When discharge conduit stop 83 abuts discharge port 29, discharge conduit inlet 12 is properly positioned to form separation gap 45. Discharge conduit stop 83 could be integral to discharge conduit 10 through a flaring or bulging of discharge conduit 10, a component mounted onto discharge conduit 10 via a gluing, swaging, heat-shrinking, or welding process etc., or simply a drop of dispensed glue.

Referring to FIG. 5A, as discharge conduit inlet 12 abuts inlet port 27, discharge conduit stop 83 is positioned at inlet port 27, restricting discharge conduit inlet 12 from protruding too deep through inlet port 27. Preferably, discharge conduit stop 83 locates discharge conduit inlet 12 within inlet port 27 such that potential liquid residue smoothly passes through micro-abrasive blasting device 75.

Referring to FIG. 5B, discharge conduit 10 is displaced so discharge conduit inlet 12 no longer abuts inlet port 27. The displacement of discharge conduit 10 is restricted by the movement of discharge conduit stop 83 to discharge port 29. Preferably, discharge conduit stop 83 locates discharge conduit inlet 12 at the geometrical center of spherical mixing chamber 23.

Referring to FIG. 5C, the extension of delivery conduit 30 external to the mixing chamber 23 facilitates a more narrow connection to the air abrasion device via a handheld pressurized-gas supply connector 55. Whereas, prior art devices connect to the mixing chamber body, this preferred embodiment connects to a narrower delivery conduit 30. Therefore, the innovative micro-abrasive blasting device 75 may be mounted as a disposable tip onto a non-disposable handheld supply connector 55. While handheld supply connector 55 is held by the user's fingertips, delivery conduit 30 of micro-abrasive blasting device 75 mounts into handheld supply connector 55 downstream of the user's fingertips. Because the innovative micro-abrasive blasting device 75 does not support the user's grip and bulky supply connector, micro-abrasive blasting device 75 can be made shorter and of less rigid material. This configuration greatly decreases the complexity and cost of the micro-abrasive blasting device 75.

Additional Embodiments

Figure 7A:
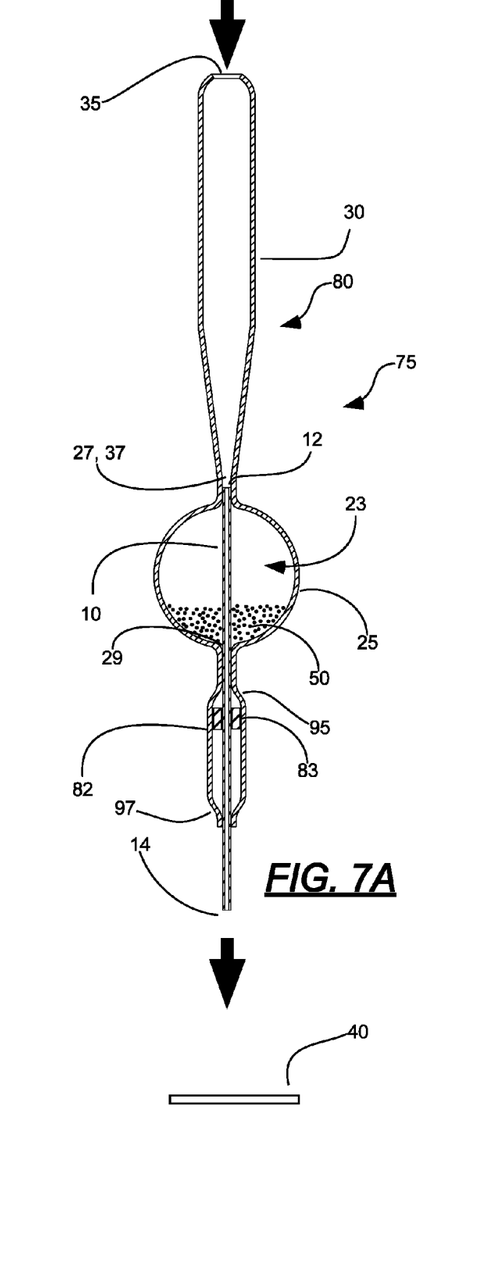
Figure 7B:
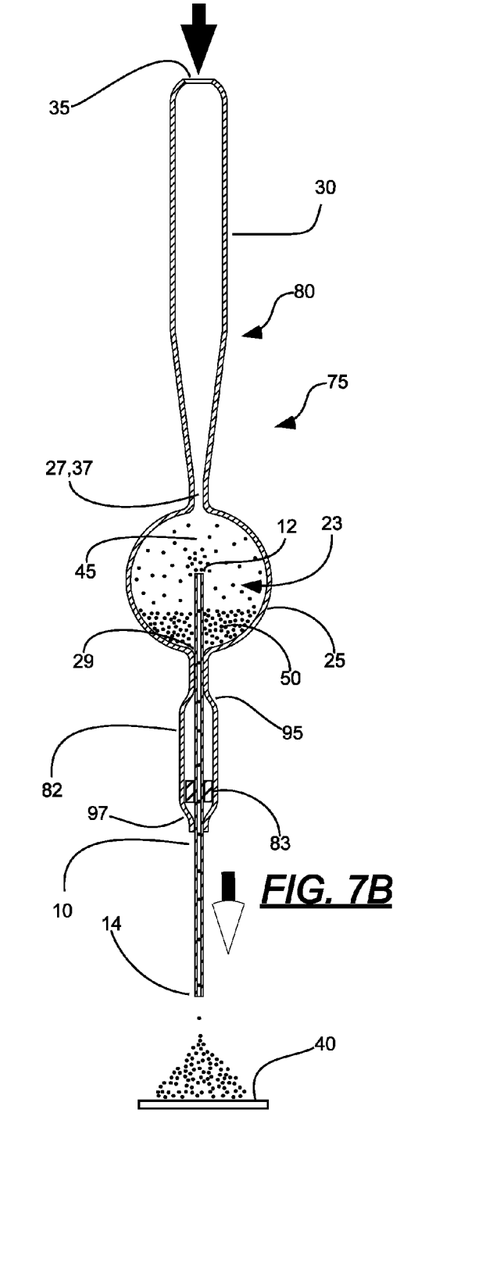

Referring to FIG. 7, contiguous pipette structure 80 is extended to include an additional hollow bulb section to form a discharge conduit bearing 82. The discharge conduit bearing 82 is a tubular extension of the discharge port 29 section, elongated from a capped position end 95 to a mixing position end 97 with a diameter equal to or greater than discharge conduit 10. Discharge conduit bearing 82 provides mechanical support to discharge conduit 10, to assure discharge conduit 10 properly displaces away from inlet port 27; a discharge conduit stop 83 is attached to discharge conduit 10 so discharge conduit stop 83 moves with discharge conduit 10 within discharge conduit bearing 82 from the capped position end 95 to the mixing position end 97. Discharge conduit stop 83 in conjunction with discharge conduit bearing 82 provides a mechanical restriction to the displacement of discharge conduit 10. When discharge conduit stop 83 abuts capped position end 95, discharge conduit inlet 12 is properly positioned to seal mixing chamber 23. When discharge conduit stop 83 abuts mixing position end 97, discharge conduit inlet 12 is properly positioned to form separation gap 45.

Figure 8:
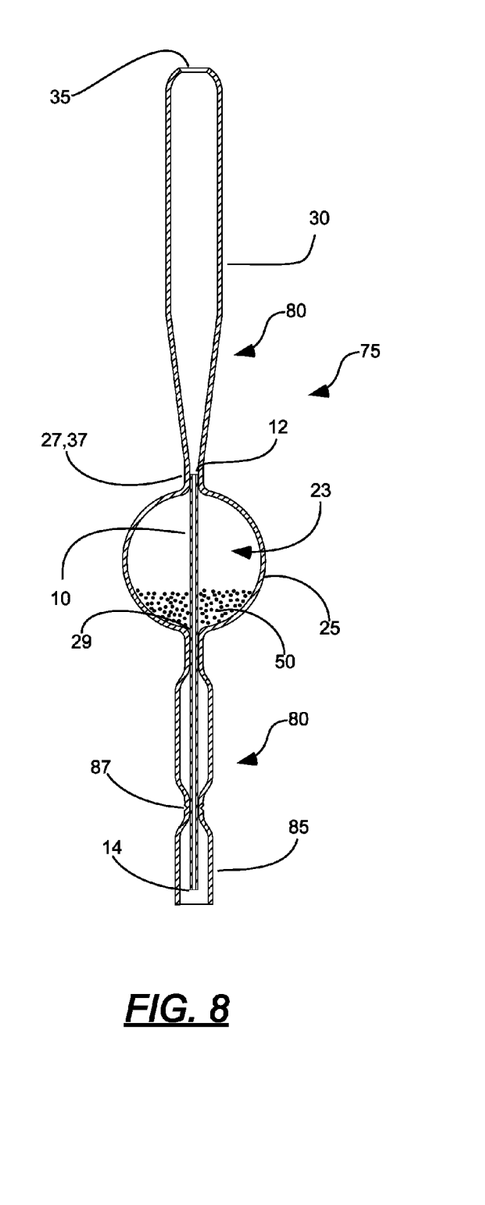
FIGS. 8 and 9 are cross-sectional views of an embodiment of the micro-abrasive blasting device with an integrated protective nozzle guard and integrated particle deflector integral to the pipette structure.
Figure 9:
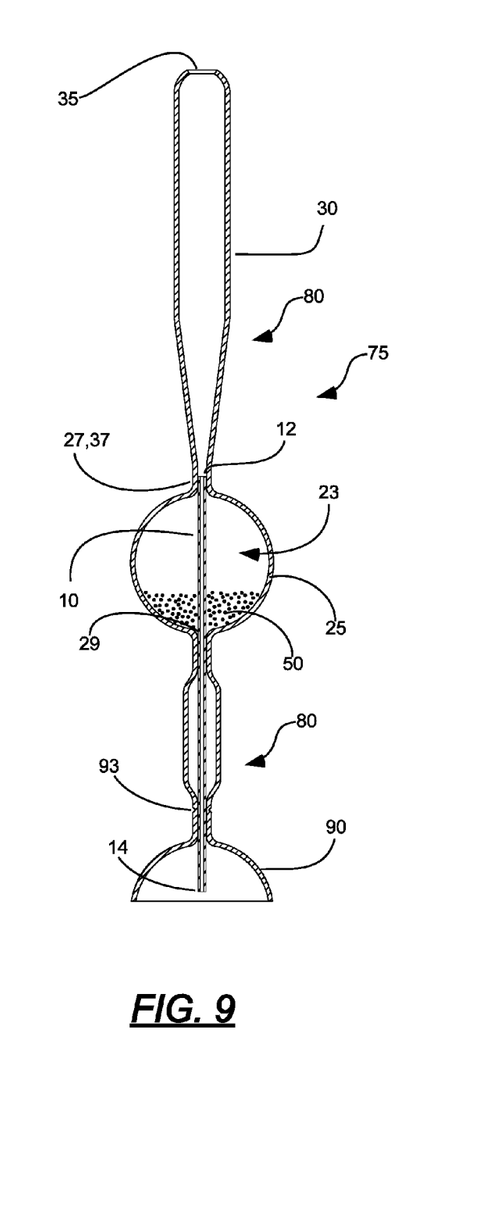

Referring to FIG. 8, contiguous pipette structure 80 is extended to include a protective nozzle guard 85. Protective nozzle guard 85 is constructed by extending pipette structure 80 so it encompasses discharge conduit outlet 14, thereby providing protection to discharge conduit 10 external to mixing chamber 23. Protection of the delivery conduit is important to prevent damage to the delivery conduit during shipping and from the delivery conduit puncturing other surrounding devices in bulk packaging. Nozzle guard 85 also prevents the delivery conduit from sticking the user when mounting micro-abrasive blasting device 75 onto the pressurized-gas connector.

Protective nozzle guard 85 may be removed prior to use, by pulling protective nozzle guard 85 coaxially to discharge conduit 10, thereby fully exposing discharge conduit 10. Preferably, perforation to pipette structure 80 is provided at nozzle guard separation point 87 as to weaken pipette structure 80 at nozzle guard separation point 87. Pulling on protective nozzle guard 85 coaxially to discharge conduit 10, causes pipette structure 80 to separate at nozzle guard separation point 87 allowing the removal of protective nozzle guard 85 to expose discharge conduit 10.

Referring to FIG. 9, contiguous pipette structure 80 is extended to include a portion of a hollow bulb section to form a particle deflector 90. Particle deflector 90 is constructed by extending pipette structure 80 to preferably form a semi-spherical bulb structure. Particle deflector 90 is positioned on discharge conduit 10 as to deflect particulate matter 50 ricocheting off the target surface during use.

Perforation to pipette structure 80 may be provided at particle deflector separation point 93 as to weaken pipette structure 80 at particle deflector separation point 93. Pulling particle deflector 90 coaxially to discharge conduit 10, separates particle deflector 90 at particle deflector separation point 93 to permit the movement of particle deflector 90 along discharge conduit 10. Preferably particle deflector 90 is positioned near discharge conduit outlet 14 as to deflect particulate matter 50 ricocheting off the target surface during use.

Of course, pipette structure 80 may be constructed to include both protective nozzle guard 85 and particle deflector 90.

Mixing Method

Referring to FIG. 3C, a separation gap 45 between the delivery conduit outlet 37 and discharge conduit inlet 12 generates rapidly expanding and contracting gas-stream that forms a pressure gradient 48. The rapid expansion of the gas-stream occurs as the gas-stream exits the narrow delivery conduit outlet 37 and expands into the wider mixing chamber 23. The rapid contraction of the gas-stream occurs as the gas-stream flows from the wider mixing chamber 23 into the narrower discharge conduit inlet 12. Because mixing chamber 23 is a closed-system, the volumetric flow rate into mixing chamber 23 must equal the volumetric flow rate out of mixing chamber 23.

Therefore, the expansion and contraction of the gas-stream across separation gap 45 is accompanied by a localized pressure gradient 48 at separation gap 45. Pressure gradient 48 across separation gap 45 within mixing chamber 23 agitates particulate matter 50 causing particulate matter 50 to aerate. The aerated particulate matter 50 particles are pulled into the gas-stream at separation gap 45, generating an abrasive laden gas stream into discharge conduit inlet 12 and out of discharge conduit outlet 14. Because pressure gradient 48 across separation gap 45 is independent of mixing chamber 23 orientations, agitation also is independent of the orientation of mixing chamber 23.

This mixing method is independent of the mixing chamber shape as long as the mixing chamber 23 is wider than the delivery conduit outlet 37 and discharge conduit inlet 12. In the absence of delivery conduit outlet 37 where delivery conduit 30 terminates at inlet port 27, this innovative mixing method still applies as pressure gradient 48 is formed across separation gap 45.

Since separation gap 45 controls the rapidness by which the gas-stream expands and contracts, the distance of separation gap 45 controls the agitation rate of particulate matter 50 within mixing chamber 23. Therefore, the quantity of particulate matter 50 introduced into the gas-steam is selectable by the position of discharge conduit inlet 12 with respect to delivery conduit outlet 37 or inlet port 27.

Summary of Claims from Parent Application Ser. No. 11/452,067 filed Jun. 13, 2006

The following are representative of claims from the parent patent application.

A micro-abrasive blasting device may comprise:

a chamber having a chamber wall and a hallow interior;

a inlet port in said chamber wall;

a discharge port in the chamber wall;

a delivery conduit elongated from a delivery conduit inlet external to said chamber to a delivery conduit outlet disposed within the chamber and extending in fluid communications through said inlet port;

a discharge conduit elongated from a discharge conduit inlet internal to the chamber to a discharge conduit outlet external to the chamber and extending in fluid communications through said discharge port;

a quantity of particulate matter disposed within said chamber; wherein a handheld pressurized-gas supply connector mounts to said delivery conduit external to the chamber.

Pressurized-gas supplied to delivery conduit inlet may pass through the delivery conduit outlet into the chamber to generate an abrasive laden gas stream out of said discharge conduit.

Said discharge conduit inlet may abut delivery conduit outlet to seal said particulate matter within said chamber.

Pressurized-gas supplied to delivery conduit inlet passes through the delivery conduit and discharge conduit without entering the chamber.

Displacement of said discharge conduit inlet away from delivery conduit outlet may unseal the chamber to allow pressurized-gas flow through the chamber to generate an abrasive laden gas stream.

The delivery conduit outlet may terminates at the inlet port of said chamber.

The chamber may be spherical.

A discharge conduit stop may be mounted to said discharge conduit is disposed within the mixing chamber to restrict the movement range of the discharge conduit.

A pre-filled disposable pipette structure for micro-abrasive blasting device may comprise:

a hollow tubular pipette structure;

said pipette structure having a hollow bulb section forming a mixing chamber;

said pipette structure further having a open ended hollow tubular delivery section smaller in diameter and contiguous with the bulb section, for delivery of pressurized-gas;

said pipette structure also having a hollow tubular discharge section smaller in diameter and contiguous with the bulb section, for discharging abrasive laden gas stream;

a quantity of particulate matter disposed within said mixing chamber;

a discharge conduit elongated from a discharge conduit inlet to a discharge conduit outlet;

wherein said discharge conduit is mounted in fluid communications through said discharge section of said pipette structure so said discharge conduit inlet is internal to the mixing chamber and discharge conduit outlet is external to the mixing chamber.

A pressurized-gas connector may mount to said delivery section.

Pressurized-gas supplied to delivery section may pass through the delivery conduit outlet into the chamber to generate an abrasive laden gas stream out of said discharge conduit.

The discharge conduit inlet may abut delivery section to seal said particulate matter within said mixing chamber.

Pressurized-gas delivered to delivery section may pass through the delivery section and discharge conduit without entering the mixing chamber.

Displacement of said discharge conduit inlet away from delivery section may unseal the mixing chamber to allow pressurized-gas flow through the mixing chamber to generate an abrasive laden gas stream.

The pipette structure may be constructed of a thermoplastic material selected from a group consisting of: polycarbonate, polyethylene, polyester, polystyrene, polypropylene, polysulfone, polyurethane, or ethylene-vinyl-acetate.

The pipette structure may be formed by extrusion blow molding in a two-piece mold.

The pipette structure may be formed by thermoforming a plastic tube.

The mixing chamber may be spherical.

The may be hollow tubular delivery section may be extended internal to said mixing chamber.

The pipette's hollow structure may be configured in cross section as selected from a group consisting of round, oval, square, rectangular and polygonal shapes.

The pipette's bulb section may have a cylindrical configuration with each end having a cone-shaped taper interfacing on one end with the delivery tube section, and on the other end with the discharge tubular section.

A method of using a handheld gas supply connector with a device for propelling particulate matter may comprise the steps of:

placing particulate matter within a mixing chamber, said mixing chamber comprising a mixing chamber wall, a inlet port at a one end of the chamber and a discharge port at an opposite end of the chamber and sized for completing at least one dental procedure;

extending a gas delivery conduit disposed external to the mixing chamber in fluid communications through said inlet port into the mixing chamber to terminate at a delivery conduit outlet;

holding a pressurized-gas supply connector in a manner by grasping said supply connector between two fingers of one hand during the application of said device for at least one dental procedure;

mounting said gas delivery conduit external to the chamber to said handheld supply connector whereby the mixing chamber is downstream of the fingers grasping location;

applying gas flow through the gas delivery conduit into the mixing chamber;

discharging a mixture of gas flow and said particulate matter through a discharge conduit in said discharge port for abrading at least one target surface of a dental procedure.

The delivery conduit outlet may terminate at said inlet port of the mixing chamber.

A method of sealing particulate matter within a device for propelling particulate matter may comprise the steps of:

placing particulate matter within a mixing chamber, said mixing chamber comprising a mixing chamber wall, a inlet port at a one end of the chamber and a discharge port at an opposite end of the chamber and sized for completing at least one dental procedure;

extending a gas delivery conduit disposed external to the mixing chamber in fluid communications through said inlet port into the mixing chamber to terminate at a delivery conduit outlet;

inserting a discharge conduit in fluid communication through said discharge port extending from a discharge conduit inlet internal to said chamber to a discharge conduit outlet external to the chamber;

positioning said discharge conduit inlet to abut said delivery conduit outlet thereby sealing particulate matter within the mixing chamber.

Pressurized-gas supplied to said gas delivery conduit may pass through the delivery conduit and discharge conduit without entering the mixing chamber.

Displacing said discharge conduit inlet away from said delivery conduit outlet may unseal the chamber.

Delivering pressurized-gas to said gas delivery conduit may pass through the delivery conduit outlet into the chamber to generate an abrasive laden gas stream out of said discharge conduit.

The delivery conduit outlet may terminate at said inlet port of the mixing chamber.

A method for generating an abrasive laden gas stream within a micro-abrasive blasting device may comprise the steps of:

placing particulate matter within a mixing chamber, said mixing chamber comprising a mixing chamber wall, a inlet port at a one end of the chamber and a discharge port at an opposite end of the chamber and sized for completing at least one dental procedure;

extending a gas delivery conduit disposed external to the mixing chamber in fluid communications through said inlet port into the mixing chamber to terminate at a delivery conduit outlet;

inserting a discharge conduit in fluid communication through said discharge port extending from a discharge conduit inlet internal to said chamber to a discharge conduit outlet external to the chamber;

positioning said discharge conduit inlet to have a separation gap with said delivery conduit outlet;

applying a gas flow through the gas delivery conduit into the mixing chamber whereby forming a pressure gradient across said separation gap;

aerating said particulate matter to mix with the said gas flow;

discharging a mixture of gas flow and said particulate matter through a discharge conduit in said discharge port for abrading at least one target surface of a dental procedure.

The delivery conduit outlet may terminate at said inlet port of the mixing chamber.

In addition to the above, the following are disclosed but may not have been claimed in the parent application:

A micro-abrasive blasting device may comprise:

a chamber having a chamber wall and a hollow interior;

an inlet port in said chamber wall;

a discharge port in the chamber wall;

a tubular delivery conduit section contiguous with said chamber wall elongated from a delivery conduit inlet external to said chamber to a delivery conduit outlet terminating at said inlet port;

a tubular discharge section contiguous with said chamber wall elongates from said discharge port external to said chamber;

a discharge conduit elongated from a discharge conduit inlet internal to the chamber to a discharge conduit outlet external to the chamber and extending through said tubular discharge section and in fluid communications with said tubular discharge section;

a quantity of particulate matter disposed within said chamber;

wherein a handheld pressurized-gas supply connector mounts to said tubular delivery conduit section external to the chamber;

wherein:

a discharge conduit stop mounted to said discharge conduit is disposed external to the mixing chamber to prevent the extraction of the discharge conduit out of the tubular delivery conduit section and tubular discharge section.

A discharge conduit bearing may comprise a elongated tubular extension of the discharge port extending from the mixing chamber, a portion of which has a diameter equal to or greater than the discharge conduit;

wherein the discharge conduit stop is disposed within the discharge conduit bearing.

A micro-abrasive blasting device may comprise:

a mixing chamber comprising a wall, an inlet port disposed in the wall and a discharge port disposed in the wall;

a delivery conduit extending from external the mixing chamber to the inlet port;

a discharge conduit extending from internal the mixing chamber, through the discharge port, to external the mixing chamber, and having a discharge conduit inlet disposed within the mixing chamber; and a discharge conduit bearing comprising a elongated tubular extension of the discharge port extending from the mixing chamber, a portion of which has a diameter equal to or greater than the discharge conduit;

wherein the discharge conduit stop is disposed within the discharge conduit bearing.

A micro-abrasive blasting device may comprise:

a mixing chamber comprising a wall, an inlet port disposed in the wall and a discharge port disposed in the wall;

a delivery conduit extending from external the mixing chamber through the inlet port to within the mixing chamber; and a discharge conduit extending from internal the mixing chamber, through the discharge port, to external the mixing chamber, and having a discharge conduit inlet disposed within the mixing chamber.

The delivery conduit may extend to within the mixing chamber.

A micro-abrasive blasting device may comprise:

a mixing chamber comprising a wall, an inlet port disposed in the wall and a discharge port disposed in the wall;

a delivery conduit extending from external the mixing chamber to the inlet port;

a discharge conduit extending from internal the mixing chamber, through the discharge port, to external the mixing chamber, having a discharge conduit inlet disposed within the mixing chamber, and having a portion including a discharge conduit outlet disposed external the mixing chamber; and a protective nozzle guard extending from the mixing chamber and encompassing the discharge conduit outlet A particle deflector may be positioned on the discharge conduit, in the form of a semi-spherical bulb structure, for deflecting particulate matter ricocheting off a target surface during use.

A micro-abrasive blasting device may comprise:
 a mixing chamber comprising a wall, an inlet port disposed in the wall and a discharge port disposed in the wall;
 a delivery conduit extending from external the mixing chamber to the inlet port;
a discharge conduit extending from internal the mixing chamber, through the discharge port, to external the mixing chamber, and having a discharge conduit inlet disposed within the mixing chamber; and
 a particle deflector positioned on the discharge conduit, in the form of a semi-spherical bulb structure, for deflecting particulate matter ricocheting off a target surface during use.

Summary of Claims from Parent Application Ser. No. 12/551,416 filed Aug. 31, 2009

The following are representative of claims from the parent patent application.

A micro-abrasive blasting device comprising:
 a mixing chamber comprising a wall, an inlet port disposed in the wall and a discharge port disposed in the wall;
 a delivery conduit extending from external the mixing chamber at least to the inlet port; and
 a discharge conduit extending from internal the mixing chamber, through the discharge port, to external the mixing chamber, and having a discharge conduit inlet disposed within the mixing chamber;
 wherein the discharge conduit is movable and,
 in a first position, the discharge conduit inlet abuts the inlet port to seal particulate matter in the chamber until use; and
 in a second position the discharge conduit inlet is displaced from the inlet port.

The discharge conduit may be disposed opposed the gas delivery conduit.

In the second position, pressurized gas supplied to the delivery conduit flows through the delivery conduit into the mixing chamber, and particulate matter in the chamber mixes with the flowing gas and is dispensed through the discharge conduit. A separation gap between the discharge conduit inlet and the inlet port controls an agitation rate of particulate matter within mixing chamber, and therefore a quantity of particulate matter introduced into the gas steam is selectable by the displaced position of discharge conduit inlet with respect to the inlet port.

The discharge conduit may be in the form of a nozzle. A nozzle guard may provide protection to the discharge conduit.

Abrasive powder may be disposed in the mixing chamber; the mixing chamber may be spherical so as to assure a distal separation between the discharge conduit inlet and the abrasive powder at all mixing chamber orientations. The discharge conduit inlet may be centered within the spherical mixing chamber.

The device may comprise a thermoplastic material selected from a group consisting of: polycarbonate, polyethylene, polyester, polystyrene, polypropylene, polysulfone, polyurethane, or ethylene-vinyl-acetate.

Advantages

From the description above, the following advantages may become evident:
 (a) Use of the delivery conduit to seal the mixing chamber, thereby:
  1. reducing the component count; and
  2. making disposable pipette structure usable for air abrasion applications.
 (b) Use the delivery conduit to create a bypass to the mixing chamber, thereby eliminating liquid entrapment within the mixing chamber.
 (c) Extending the delivery conduit external to the mixing chamber, thereby making the device adaptable to a handheld gas supply connector and standard tube fitting.
 (d) Generation of a localized pressure gradient within the mixing chamber to generate and control powder agitation rates.
 (e) Use of a spherical mixing chamber to deliver consistent powder perturbation at all mixing chamber orientations.
 (f) Simplified construction using contiguous pipette structure fabricated to form the body of the micro-abrasion device.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

Summary, Ramification, and Scope

The present invention may accomplish the above-stated objectives, as well as others, as may be determined by a fair reading and interpretation of the entire specification.

Accordingly, the reader will see that the micro-abrasive blasting device may have reduced components, simplified construction, enhanced mixing methodology, and mountable to handheld gas supply connector.

Furthermore, the micro-abrasive blasting device has the additional advantages in that
 it provides a more narrow pressurized-gas supply connection.
 it provides a sealed device that is resistant to fluid contamination.
 it provides a reliable device that delivers a consistent quantity of abrasive at any orientation.
 it provides the user with ability to select powder delivery rates by external manipulation of the discharge conduit position.
 it provides a simplified construction methodology which reduces the manufacturing cost of the product.

Thus the scope of the invention should be determined by the appended claims and their legal equivalents, rather than by the examples given.

What is claimed is:

1. A method of making a micro-abrasive blasting device pipette component comprising a mixing chamber having a wall, an inlet port disposed in the wall, and a discharge port disposed in the wall, the method comprising:
 forming a gas delivery conduit extending from external the mixing chamber to the inlet port, and having an inlet end;

forming a discharge conduit extending from the discharge port, to external the mixing chamber, and having an outlet end; and sealing one of the inlet and outlet ends; and with one of the inlet and outlet ends sealed to entrap pressurized gas, performing a blow-molding process for forming the pipette component.

2. The method of claim 1, wherein the gas delivery conduit is narrower than the mixing chamber.

3. The method of claim 1, wherein the sealed end is the inlet end, and further comprising:

puncturing or cutting the sealed end to permit air flow into micro-abrasive blasting device.

4. The method of claim 3, wherein puncturing or cutting the sealed end is effected by mounting the device to a pressurized gas connector.

5. The method of claim 1, wherein:

the pipette component is formed by extrusion blow molding in a two-piece mold.

6. The method of claim 1, wherein:

the pipette component is formed by thermoforming a plastic tube.

7. The method of claim 1, wherein:

the mixing chamber comprises bulb section having a cylindrical configuration with two ends, each end having a cone-shaped taper; and interfacing on one end with the gas delivery conduit, and on the other end with the discharge conduit.

8. The method of claim 1, further comprising:

constructing the micro-abrasive blasting device pipette component out of a continuous tubing.

9. The method of claim 1, wherein:

the device comprises a thermoplastic material selected from a group consisting of: polycarbonate, polyethylene, polyester, polystyrene, polypropylene, polysulfone, polyurethane, or ethylene-vinyl-acetate.

* * * * *